(12) United States Patent
Ellegala

(10) Patent No.: US 12,279,787 B2
(45) Date of Patent: Apr. 22, 2025

(54) SPINAL SURGERY METHOD

(71) Applicant: Misonix, LLC, Farmingdale, NY (US)

(72) Inventor: Dilantha B. Ellegala, Paradise Valley, AZ (US)

(73) Assignee: Misonix, LLC, Farmingdale, NY (US)

(*) Notice: Subject to any disclaimer, the term of this patent is extended or adjusted under 35 U.S.C. 154(b) by 894 days.

(21) Appl. No.: 17/158,596

(22) Filed: Jan. 26, 2021

(65) Prior Publication Data
US 2021/0267622 A1    Sep. 2, 2021

Related U.S. Application Data

(60) Provisional application No. 62/982,503, filed on Feb. 27, 2020.

(51) Int. Cl.
*A61B 17/32* (2006.01)
*A61B 17/00* (2006.01)

(52) U.S. Cl.
CPC ......... *A61B 17/320068* (2013.01); *A61B 2017/00261* (2013.01); *A61B 2017/320004* (2013.01);
(Continued)

(58) Field of Classification Search
CPC A61F 2/44; A61B 17/00; A61B 17/32; A61B 17/322; A61B 17/320068
See application file for complete search history.

(56) References Cited

U.S. PATENT DOCUMENTS 2,349,959 A  5/1944  Edward
2,753,666 A  7/1956  Sasse
(Continued)

FOREIGN PATENT DOCUMENTS

CN    109152577 B    1/2022
EP    2635192 B1     3/2019
(Continued)

OTHER PUBLICATIONS

SonicOne O.R., Ultrasonic Surgical Debridement. Brochure [online]. Misonix Ultrasonic Surgical Devices, 2012. Retrieved from the Internet: URL: https://web.archive.org/web/20150218182717/ http://www.misonix.com:80/wp-content/uploads/2013/11/SO-OR_2003-12_REV_A_SonicOne_OR_Brochure.pdf, 6 Pages.
(Continued)

*Primary Examiner* — Christopher J Beccia
(74) *Attorney, Agent, or Firm* — COOLEY LLP

(57) ABSTRACT

A discectomy method entails removing at least a portion of a spinal lamina to form an access path in a patient. A surgical instrument is inserted along the path and a distal end of the instrument is placed in operative contact with herniated or bulging disc material of a spinal disc. The instrument is operated to remove the herniated or bulging disc material, to thereby space a remaining portion of the spinal disc from spinal nerves. A tip of an ultrasonic surgical probe is then placed into contact with an outer surface of the remaining portion of the spinal disc, and an ultrasonic mechanical standing wave generated in the probe while maintaining the operative tip in contact with the outer surface to harden the wall surface and thereby reduce chances of disc herniation at the outer surface.

6 Claims, 3 Drawing Sheets

(52) U.S. Cl.
CPC ............... *A61B 2017/32007* (2017.08); *A61B 2017/320082* (2017.08); *A61B 2017/320084* (2013.01)

(56) References Cited

U.S. PATENT DOCUMENTS

| | | | |
|---|---|---|---|
| 3,368,280 A | 2/1968 | Friedman et al. | |
| 3,680,610 A | 8/1972 | Lindgren | |
| 3,805,787 A | 4/1974 | Banko | |
| 4,188,952 A | 2/1980 | Loschilov et al. | |
| 4,425,115 A | 1/1984 | Wuchinich | |
| 4,804,364 A | 2/1989 | Dieras et al. | |
| 4,988,334 A | 1/1991 | Hornlein et al. | |
| 5,163,433 A | 11/1992 | Kagawa et al. | |
| 5,176,677 A | 1/1993 | Wuchinich | |
| 5,180,363 A | 1/1993 | Idemoto et al. | |
| 5,222,937 A | 6/1993 | Kagawa | |
| 5,261,922 A | 11/1993 | Hood | |
| 5,312,329 A | 5/1994 | Beaty et al. | |
| 5,342,380 A | 8/1994 | Hood | |
| 5,465,468 A | 11/1995 | Manna | |
| 5,484,398 A | 1/1996 | Stoddard | |
| 5,517,889 A | 5/1996 | Logan | |
| 5,527,273 A | 6/1996 | Manna et al. | |
| 5,531,597 A | 7/1996 | Foulkes et al. | |
| 5,695,510 A | 12/1997 | Hood | |
| 5,769,211 A | 6/1998 | Manna et al. | |
| 5,906,595 A | 5/1999 | Powell et al. | |
| 5,935,142 A | 8/1999 | Hood | |
| 5,935,143 A | 8/1999 | Hood | |
| 5,976,105 A | 11/1999 | Marcove et al. | |
| 6,033,375 A | 3/2000 | Brumbach | |
| 6,036,667 A | 3/2000 | Manna et al. | |
| 6,256,859 B1 | 7/2001 | Stoddard et al. | |
| 6,270,471 B1 | 8/2001 | Hechel et al. | |
| 6,352,532 B1 | 3/2002 | Kramer et al. | |
| 6,375,648 B1 | 4/2002 | Edelman et al. | |
| 6,379,371 B1 | 4/2002 | Novak et al. | |
| 6,436,114 B1 | 8/2002 | Novak et al. | |
| 6,443,969 B1 | 9/2002 | Novak et al. | |
| 6,454,730 B1 | 9/2002 | Hechel et al. | |
| 6,461,314 B1 | 10/2002 | Pant et al. | |
| 6,492,762 B1 | 12/2002 | Pant et al. | |
| 6,494,714 B1 | 12/2002 | Copeland | |
| 6,582,440 B1 | 6/2003 | Brumbach | |
| 6,602,248 B1 | 8/2003 | Sharps et al. | |
| 6,613,056 B1 | 9/2003 | Brumbach et al. | |
| 6,648,839 B2 | 11/2003 | Manna et al. | |
| 6,736,814 B2 | 5/2004 | Manna et al. | |
| 6,787,974 B2 | 9/2004 | Fjield et al. | |
| 6,799,729 B1 | 10/2004 | Voic | |
| 6,869,439 B2 | 3/2005 | White et al. | |
| 6,902,536 B2 | 6/2005 | Manna et al. | |
| 7,025,735 B2 | 4/2006 | Soring et al. | |
| 7,223,267 B2 | 5/2007 | Isola et al. | |
| 7,431,704 B2 | 10/2008 | Babaev | |
| 7,442,168 B2 | 10/2008 | Novak et al. | |
| 7,494,488 B2 | 2/2009 | Weber | |
| 7,522,955 B2 | 4/2009 | Rontal | |
| 7,608,054 B2 | 10/2009 | Söring et al. | |
| 7,717,913 B2 | 5/2010 | Novak et al. | |
| 7,776,027 B2 | 8/2010 | Manna et al. | |
| 7,785,278 B2 | 8/2010 | Babaev | |
| D627,463 S | 11/2010 | Voic et al. | |
| 7,905,854 B2 | 3/2011 | Hazut et al. | |
| 7,931,611 B2 | 4/2011 | Novak et al. | |
| D644,326 S | 8/2011 | Voic et al. | |
| 8,025,672 B2 | 9/2011 | Novak et al. | |
| 8,109,925 B2 | 2/2012 | Voic et al. | |
| 8,221,424 B2 | 7/2012 | Cha | |
| D667,117 S | 9/2012 | Darian et al. | |
| 8,343,178 B2 | 1/2013 | Novak et al. | |
| 8,348,880 B2 | 1/2013 | Messerly et al. | |
| 8,353,912 B2 | 1/2013 | Darian et al. | |
| D680,218 S | 4/2013 | Darian et al. | |
| 8,430,897 B2 | 4/2013 | Novak et al. | |
| 8,562,547 B2 | 10/2013 | Babaev | |
| 8,659,208 B1 | 2/2014 | Rose et al. | |
| 8,690,783 B2 | 4/2014 | Sinelnikov | |
| 8,698,377 B2 | 4/2014 | Sinelnikov | |
| 8,814,870 B2 | 8/2014 | Paraschiv et al. | |
| 8,888,783 B2 | 11/2014 | Young | |
| 8,894,673 B2 | 11/2014 | Darian | |
| 8,961,547 B2 | 2/2015 | Dietz et al. | |
| 9,070,856 B1 | 6/2015 | Rose et al. | |
| 9,211,137 B2 | 12/2015 | Voic | |
| 9,226,767 B2 | 1/2016 | Stulen et al. | |
| 9,320,528 B2 | 4/2016 | Voic et al. | |
| 9,387,005 B2 | 7/2016 | Voic | |
| 9,603,656 B1 | 3/2017 | Germain et al. | |
| 9,622,766 B2 | 4/2017 | Voic | |
| 9,636,187 B2 | 5/2017 | Voic | |
| 9,693,792 B2 | 7/2017 | Novak et al. | |
| 9,763,673 B2 | 9/2017 | Young | |
| 9,861,446 B2 | 1/2018 | Lang | |
| 9,872,697 B2 | 1/2018 | Voic | |
| 9,949,751 B2 * | 4/2018 | Voic | A61B 17/320068 |
| 9,962,182 B2 | 5/2018 | Dietz et al. | |
| 10,016,208 B2 | 7/2018 | Gouery et al. | |
| 10,076,349 B2 | 9/2018 | Voic | |
| 10,092,308 B2 | 10/2018 | Mikus et al. | |
| 10,092,741 B2 | 10/2018 | Darian | |
| 10,117,666 B2 | 11/2018 | Voic | |
| 10,182,837 B2 | 1/2019 | Isola et al. | |
| 10,206,704 B2 | 2/2019 | Voic et al. | |
| 10,299,809 B2 | 5/2019 | Mikus et al. | |
| 10,398,463 B2 | 9/2019 | Darian et al. | |
| 10,398,465 B2 | 9/2019 | Darian | |
| 10,405,875 B2 | 9/2019 | Voic et al. | |
| 10,463,381 B2 | 11/2019 | Voic et al. | |
| 10,470,788 B2 | 11/2019 | Sinelnikov | |
| 10,470,789 B2 | 11/2019 | Mikus et al. | |
| 10,471,281 B2 | 11/2019 | Mikus | |
| 10,543,012 B2 | 1/2020 | Pantano | |
| 10,588,691 B2 | 3/2020 | Pellegrino et al. | |
| 10,639,733 B2 | 5/2020 | Campbell et al. | |
| 10,687,824 B2 | 6/2020 | Shiels et al. | |
| 10,835,276 B2 | 11/2020 | Voic et al. | |
| 10,842,587 B2 | 11/2020 | Mikus et al. | |
| 11,007,308 B2 | 5/2021 | Payne et al. | |
| 11,298,434 B2 | 4/2022 | Isola et al. | |
| 11,324,531 B2 | 5/2022 | Voic et al. | |
| 11,389,183 B2 | 7/2022 | Voic et al. | |
| 11,406,413 B2 | 8/2022 | Voic et al. | |
| 11,540,853 B2 | 1/2023 | Voic et al. | |
| 11,672,558 B2 | 6/2023 | Voic | |
| 11,737,775 B2 | 8/2023 | Voic et al. | |
| 11,950,790 B2 | 4/2024 | Voic | |
| 12,011,190 B2 | 6/2024 | Theodore et al. | |
| 2001/0029370 A1 | 10/2001 | Hodva et al. | |
| 2003/0212395 A1 | 11/2003 | Woloszko et al. | |
| 2004/0265776 A1 | 12/2004 | Tipton et al. | |
| 2005/0033292 A1 | 2/2005 | Teitelbaum et al. | |
| 2006/0030797 A1 | 2/2006 | Zhou et al. | |
| 2006/0235305 A1 | 10/2006 | Cotter et al. | |
| 2006/0241533 A1 | 10/2006 | Geller | |
| 2007/0060926 A1 | 3/2007 | Escaf | |
| 2007/0213734 A1 | 9/2007 | Bleich et al. | |
| 2008/0015551 A1 | 1/2008 | Feine | |
| 2008/0057470 A1 | 3/2008 | Levy et al. | |
| 2008/0058775 A1 | 3/2008 | Darian et al. | |
| 2008/0108985 A1 | 5/2008 | Konesky | |
| 2008/0183173 A1 | 7/2008 | Jozat | |
| 2008/0234709 A1 | 9/2008 | Houser | |
| 2008/0234710 A1 | 9/2008 | Neurohr et al. | |
| 2009/0143678 A1 | 6/2009 | Keast et al. | |
| 2009/0247937 A1 | 10/2009 | Rontal | |
| 2010/0022944 A1 | 1/2010 | Wilcox | |
| 2010/0049188 A1 | 2/2010 | Nelson et al. | |
| 2010/0076349 A1 | 3/2010 | Babaev | |
| 2011/0092880 A1 * | 4/2011 | Gertner | A61N 7/02 604/20 |
| 2011/0105958 A1 | 5/2011 | Babaev | |
| 2011/0160624 A1 | 6/2011 | Babaev | |

(56) References Cited

U.S. PATENT DOCUMENTS

| | | |
|---|---|---|
| 2011/0264090 A1 | 10/2011 | Shadduck et al. |
| 2012/0014868 A1 | 1/2012 | Roy |
| 2012/0053492 A1 | 3/2012 | Chang et al. |
| 2013/0103021 A1 | 4/2013 | Germain et al. |
| 2013/0123774 A1 | 5/2013 | Zadeh |
| 2013/0226042 A1 | 8/2013 | Novak et al. |
| 2013/0231528 A1 | 9/2013 | Voic |
| 2013/0245638 A1 | 9/2013 | Horton et al. |
| 2014/0107537 A1 | 4/2014 | Beaupre |
| 2014/0180002 A1 | 6/2014 | Voic |
| 2014/0277030 A1 | 9/2014 | Lauchner |
| 2014/0277034 A1 | 9/2014 | Darian |
| 2014/0350567 A1 | 11/2014 | Schmitz et al. |
| 2014/0358043 A1 | 12/2014 | Akagane |
| 2015/0066032 A1 | 3/2015 | Young |
| 2015/0088137 A1 | 3/2015 | Manna |
| 2015/0094723 A1 | 4/2015 | Darian |
| 2015/0157387 A1 | 6/2015 | OuYANG et al. |
| 2015/0164534 A1 | 6/2015 | Felder et al. |
| 2015/0297246 A1 | 10/2015 | Patel et al. |
| 2016/0022283 A1 | 1/2016 | Wallace et al. |
| 2016/0135835 A1 | 5/2016 | Onuma |
| 2016/0166276 A1 | 6/2016 | Huang et al. |
| 2016/0175150 A1 | 6/2016 | Banko |
| 2016/0206302 A1 | 7/2016 | Eckermann |
| 2016/0222526 A1 | 8/2016 | Rubinsky et al. |
| 2016/0331439 A1 | 11/2016 | Winkelman et al. |
| 2016/0354559 A1 | 12/2016 | Gavini et al. |
| 2017/0340339 A1 | 11/2017 | Madan et al. |
| 2018/0008138 A1 | 1/2018 | Thommen et al. |
| 2019/0000553 A1 | 1/2019 | Lightcap et al. |
| 2020/0121374 A1 | 4/2020 | McGahan et al. |
| 2020/0246056 A1 | 8/2020 | Bonn |
| 2020/0405501 A1* | 12/2020 | Orozco Castillo ......... A61B 17/7086 |
| 2021/0145531 A1 | 5/2021 | Gee et al. |
| 2023/0048993 A1 | 2/2023 | Levy et al. |
| 2023/0144990 A1 | 5/2023 | Voic et al. |
| 2023/0210549 A1 | 7/2023 | Voic et al. |

FOREIGN PATENT DOCUMENTS

| | | |
|---|---|---|
| JP | H0614934 A | 1/1994 |
| JP | H10127682 A | 5/1998 |
| KR | 20120093654 A | 8/2012 |
| WO | WO-2004060141 A2 | 7/2004 |
| WO | WO-2007049718 A1 | 5/2007 |
| WO | WO-2008014258 A2 | 1/2008 |
| WO | WO-2008017909 A1 | 2/2008 |
| WO | WO-2008118708 A2 | 10/2008 |
| WO | WO-2008118709 A1 | 10/2008 |
| WO | WO-2009035508 A1 | 3/2009 |
| WO | WO-2009098664 A2 | 8/2009 |
| WO | WO-2009105628 A2 | 8/2009 |
| WO | WO-2010109447 A1 | 9/2010 |
| WO | WO-2013062118 A1 | 5/2013 |
| WO | WO-2014024550 A1 | 2/2014 |
| WO | WO-2015045198 A1 | 4/2015 |
| WO | WO-2015046349 A1 | 4/2015 |
| WO | WO-2015145444 A2 | 10/2015 |
| WO | WO-2017180493 A1 | 10/2017 |
| WO | WO-2017192288 A1 | 11/2017 |
| WO | WO-2018022311 A1 | 2/2018 |
| WO | WO-2018165004 A1 | 9/2018 |
| WO | WO-2019095831 A1 | 5/2019 |
| WO | WO-2019204641 A1 | 10/2019 |
| WO | WO-2022087523 A1 | 4/2022 |
| WO | WO-2022245499 A1 | 11/2022 |
| WO | WO-2023018863 A1 | 2/2023 |
| WO | WO-2023130103 A1 | 7/2023 |

OTHER PUBLICATIONS

SonicOne Plus, Ultrasonic Debridement System. Brochure [online]. Misonix Ultrasonic Surgical Devices, 2013. Retrieved from the Internet: URL: https://pdf.medicalexpo.com/pdf/misonix/sonicone-plus/79244-106567.html, 4 pages.

* cited by examiner

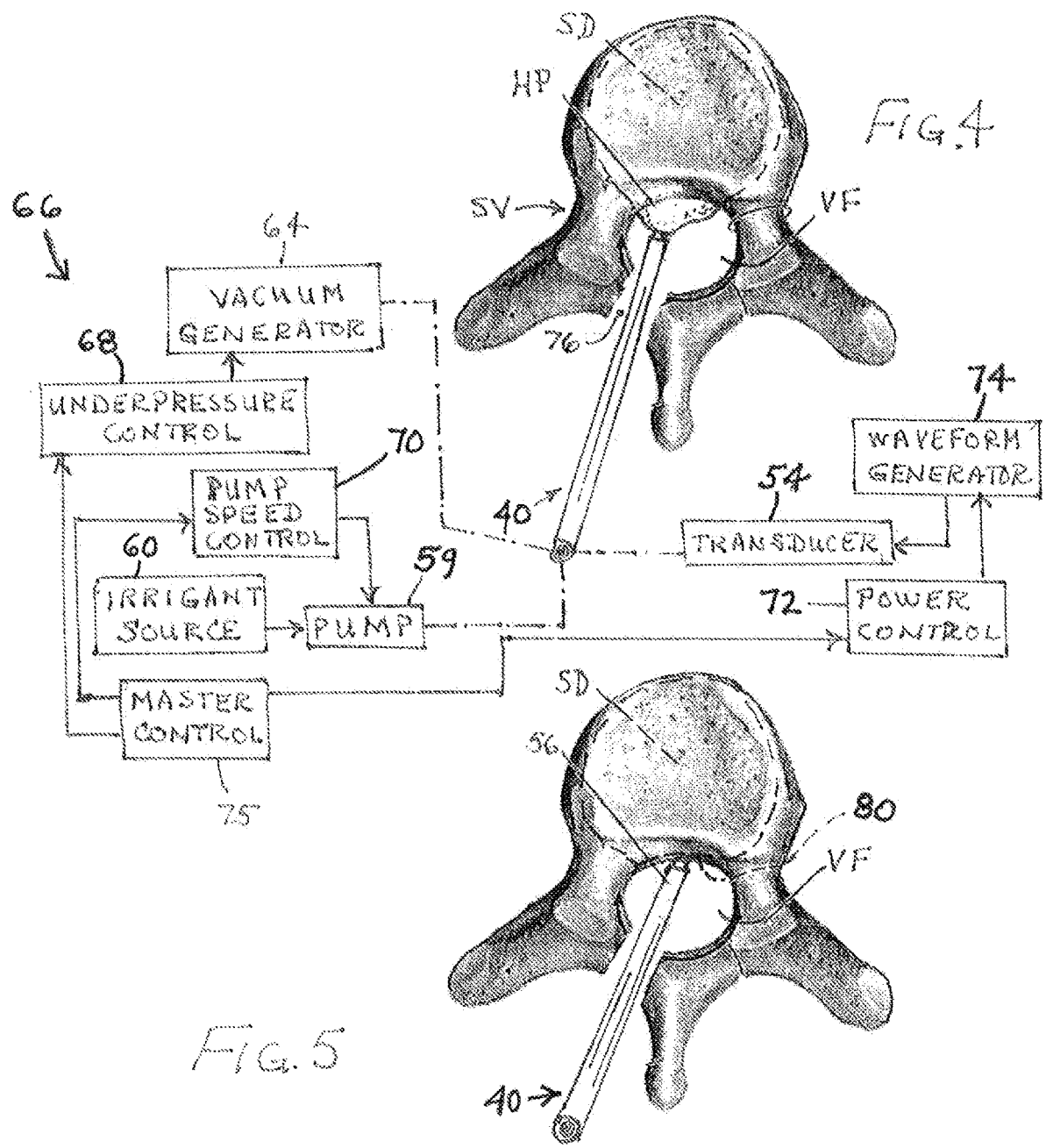

SPINAL SURGERY METHOD

BACKGROUND OF THE INVENTION

This invention relates to surgical procedures commonly known as discectomies. More particularly, this invention relates to a surgical procedure for treatment of herniated and bulging discs.

The spinal column is comprised in part of bones or vertebrae and in part of fibrous discs that are disposed between the vertebrae. The discs normally function as cushions separating the vertebrae. With age, owing to a drying of the disks, the cushioning effect may be reduced. More significantly for patient treatment purposes, injury can cause a disc to bulge and press on the nerve root leaving the spinal column, possibly causing extreme pain.

More specifically, when the outer wall of a disc, called the annulus fibrosis, becomes weakened through age or injury, it may tear allowing the soft inner part of the disc, the nucleus pulposus, to bulge out. This is called disc herniation, disc prolapse, or a slipped or bulging disc. In a bulging disc the annulus is still intact but lax and the disc pushes the intact annulus out. In a herniated disc there is a tear in the annulus and a fragment is extruded out. Both are candidates for this procedure if the patient is symptomatic from compression.

Once the inner disc material extends out past the regular outer margin of the disc, it can press against very sensitive nerve tissue in the spine. The "bulging" or "herniated" disc can compress or even damage the nerve tissue, and this can cause weakness, tingling, or pain in the back area and into one or both legs, arms or thorax depending on the location of the pathology.

A discectomy is a surgical procedure generally to remove part of an intervertebral disc that is putting pressure on a nerve as it leaves the spinal column. The procedure is most commonly performed on lumbar discs (located in the lower back) creating leg pain. However, it may also be used for cervical discs or thoracic discs.

Open discectomy is usually performed under general anesthesia (the patient is unconscious) and typically requires a one-day hospital stay. It is performed while the patient is lying face down or in a kneeling position. During the procedure, the surgeon will make an approximate one to four-inch incision in the skin over the affected area of the spine. Muscle tissue is disconnected from the bone at the affected disc and retractors hold the muscle and skin away from the spinal column at the surgical site so the surgeon has a clear view of the lamina and interspace of the herniated disc. In some cases bone and ligaments particularly including vertebral lamina may have to be removed for the surgeon to be able to visualize and then gain access to the bulging disc without damaging the nerve tissue, this is called a hemilaminectomy or laminotomy, depending on how much bone is removed. Access to the spinal canal may also be performed through sequentially dilating tubes through which the surgery is performed. The surgical procedural details below are regardless of the access method used.

Once the surgeon can visualize the vertebrae, disc and other surrounding structures, he or she will remove the section of the disc that is protruding from the disc wall, typically using a so-called Pituitary Rongeurs or grasping forceps, and any other disc fragments that may have been expelled from the disc or in the disc space itself. This is often done under magnification. Nothing is used to replace the disc material that is removed. The muscle and skin incision is then closed with sutures and the patient is taken to a recovery room.

The most common problem of a discectomy is that there is a chance that another fragment of disc will herniate and cause similar symptoms post surgery. This is a so-called recurrent disc herniation, and the risk of this occurring is about 10-15%

OBJECTS OF THE INVENTION

It is an object of the present invention to provide an improved discectomy procedure.

A more particular object of the present invention is to provide a discectomy procedure that reduces the rate and risk of recurrence.

Another object of the present invention is to provide a surgical discectomy method that is at least partially quicker and easier to carry out than conventional techniques.

Yet another object of the present invention is to provide a surgical discectomy method that may be carried out in a minimally invasive procedure.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A discectomy method in accordance with the present invention comprises (a) removing at least a portion of a spinal lamina to form an access path in a patient. (b) inserting a surgical instrument along the path so that a distal end of the surgical instrument is operatively engageable with a herniated or bulging portion of a spinal disc, (c) operating the surgical instrument to remove the herniated or bulging disc material, to thereby space a remaining portion of the spinal disc from spinal nerves, (d) placing an operating tip of an ultrasonic surgical probe into contact with an outer surface of the remaining portion of the spinal disc, and (e) generating an ultrasonic mechanical standing wave in the ultrasonic surgical probe while maintaining the operative tip in contact with the outer surface to harden the outer surface and thereby reduce chances of disc herniation at the outer surface.

The generating of the ultrasonic mechanical standing wave in the ultrasonic surgical probe is preferably carried out at an ultrasonic vibratory power sufficiently low to avoid significant damage to the spinal disc material. In addition, the generating of the ultrasonic mechanical standing wave in the ultrasonic surgical probe is typically carried out with minimal or no irrigation and little or no suction applied to the outer surface of the disc. The hardening of the disc's outer surface formed by the removal of the herniated or bulging disc material is believed to result from protein denaturing in response to the application of ultrasonic vibratory energy. Preferably, the applied energy is not great enough to cause significantly detrimental disc damage.

In one contemplated embodiment of the present invention, the surgical instrument that fragments and removes the herniated or bulging portion of the target disc is an ultrasonic surgical instrument different from the ultrasonic surgical probe that hardens the surface or wall of the remaining disc material. In that case, the surgical instrument is withdrawn from the patient after removing of the herniated or bulging disc material, the ultrasonic surgical probe being inserted into the patient along the access path after removal of the surgical instrument.

The operation to remove the herniated or bulging disc material includes feeding irrigation fluid and applying suction to the operating tip during the removal of the herniated or bulging material. The irrigation serves in part to cool the ultrasonic probe as well as a surrounding sheath, thereby avoiding heat damage to adjacent tissues, but also provides a liquid matrix or carrier to generate a slurry of debris from the surgical site. The generating of the ultrasonic mechanical standing wave in the ultrasonic surgical probe to harden the disc wall is carried out with substantially less irrigation and substantially less suction than that applied to the outer surface of the disc during operating of the ultrasonic surgical instrument.

Pursuant to an ancillary feature of the present invention, the selective removal of vertebral bone includes operating an ultrasonic abrading or incising instrument different from both the ultrasonic surgical instrument and the ultrasonic surgical probe.

In accordance with a preferred embodiment of the present invention, the disc-material-removal surgical instrument and the disc-hardening ultrasonic surgical probe are one and the same instrument. Thus the operating tip of the latter is the distal tip of the former. Operating the singular surgical instrument to remove the herniated or bulging disc material includes feeding irrigation fluid and applying suction to the operating tip during the removal of the herniated or bulging disc material. The method of this preferred embodiment further comprises substantially reducing both a feeding rate of the irrigation fluid and a degree of applied suction during the generating of the ultrasonic mechanical standing wave to harden the outer surface of the disc. Specifically, the feeding rate of the irrigation fluid and the degree of applied suction are respectively reduced at least 80% relative to a feeding rate of the irrigation fluid and a degree of applied suction during the operating of the surgical instrument to remove the herniated or bulging disc material. In addition, power supplied to the ultrasonic surgical probe is substantially reduced during the generating of the ultrasonic mechanical standing wave to harden the disc's outer surface. Specifically, the power of ultrasonic vibration of the ultrasonic surgical probe during the generating of the ultrasonic mechanical standing wave to harden the disc's outer surface is less than 20%, preferably much less than 20%, of the power of ultrasonic vibration of the ultrasonic surgical probe during the operating thereof to remove the herniated or bulging disc material.

BRIEF DESCRIPTION OF THE DRAWINGS

FIG. 4 is partially a schematic top view of an upper spinal vertebra shown in FIG. 3 and a distal end portion of the probe of FIG. 2 and partially a block diagram, showing a subsequent step in the surgical method of the present invention.

FIG. 5 is a schematic top view of the upper spinal vertebra shown in FIG. 4 and the distal end portion of the probe of FIGS. 2 and 3, showing a further step in the surgical method of the present invention.

DETAILED DESCRIPTION

Figure 1:
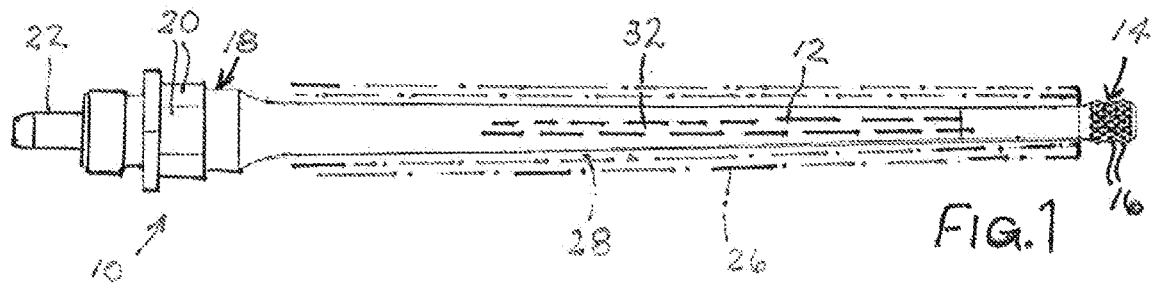
FIG. 1 is a side elevational view of an ultrasonic bone shaving probe for performing a laminectomy in a surgical method in accordance with the present invention.

As depicted in FIG. 1, an ultrasonic probe or instrument 10 for performing a laminectomy includes a shaft 12 and a head 14 provided along a cylindrical lateral surface (not separately designated) with an array of teeth 16. At a proximal end, probe 10 includes an enlarged shank portion 18 with wrench flats 20 and an externally threaded connector 22 for fastening the probe to a vibration engine comprising an ultrasonic transducer 24 (FIG. 3) typically of the piezo-electric or magnetostrictive variety. Probe 10 is used with a sheath 26 that, together with an outer surface of the probe, defines a cylindrical space 28 for conducting liquid coolant from an irrigant source 30 (FIG. 3) to the probe head 14. Probe 10 has a central lumen 32 connectable to a suction source or vacuum generator 34 (FIG. 3) and communicating with apertures (not shown) exemplarily in the lateral surface of head 14 for the removal of a slurry of irrigant and organic debris from a surgical site. A pump 36 moves the liquid coolant from source 30 through cylindrical space 28 to probe head 14. Suction source 30 removes a slurry of disc debris and irrigant from the surgical site through lumen 32.

Figure 2:
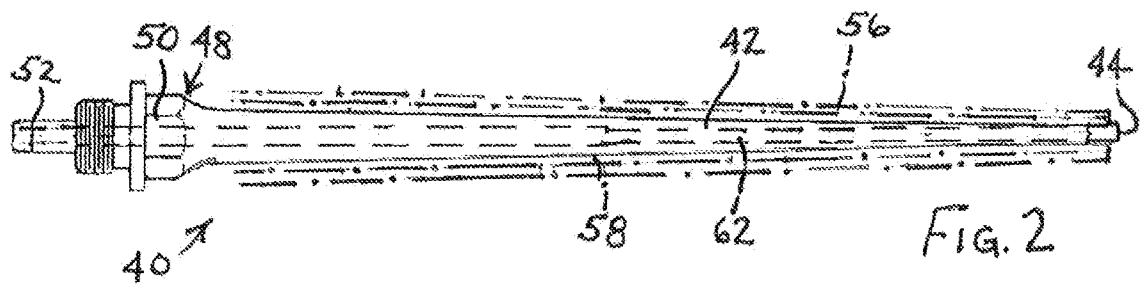
FIG. 2 a side elevational view of an ultrasonic probe for removing herniated or bulging disc material and hardening a portion of remaining disc in accordance with the surgical method of the present invention.

As depicted in FIG. 2, an ultrasonic probe or instrument 40 for fragmenting and removing herniated or bulging disc material and preferably also for subsequently hardening a surface of a resulting disc remnant includes a shaft 42 and a distal or operative tip 44 provided. At a proximal end, probe 40 includes an enlarged shank portion 48 with wrench flats 50 and an externally threaded connector 52 for fastening the probe to a vibration engine comprising an ultrasonic transducer 54 (FIG. 4), exemplarily piezoelectric or magnetostrictive. Probe 40 is used with a sheath 56 that, together with an outer surface of the probe, defines a cylindrical space 58 for conducting liquid coolant moved by a pump 59 from an irrigant source 60 (FIG. 4) to the probe's distal or operative tip 44. Probe 40 has a central lumen 62 connectable to a suction source or vacuum generator 64 (FIG. 4) at a proximal end (not designated) and communicating at a distal end with an aperture (not shown) disposed in distal or operative tip 44, in a transverse plane to a longitudinal probe axis (not indicated), for the removal of a slurry of irrigant and debris from surgical site.

As illustrated in FIG. 4, a support system 66 for probe or instrument 40 includes an under-pressure control 68 for use by an operator or surgeon to modulate the strength of the suction applied by vacuum generator 64, a pump speed control 70 for use by the surgeon to adjust the rate of liquid delivery through cylindrical space 58 to probe tip 44, and a power control 72 for use by the surgeon to alternatively increase and decrease the ultrasonic motional amplitude fed by a waveform generator 74 to transducer 54. A master control 75 may be connected to vacuum generator 64, pump 59, and waveform generator 74 directly or, alternatively, indirectly via controls 68, 70 and 72 for simultaneously modifying all three operating parameters, suction level, irrigation rate, and power magnitude.

Figure 3:
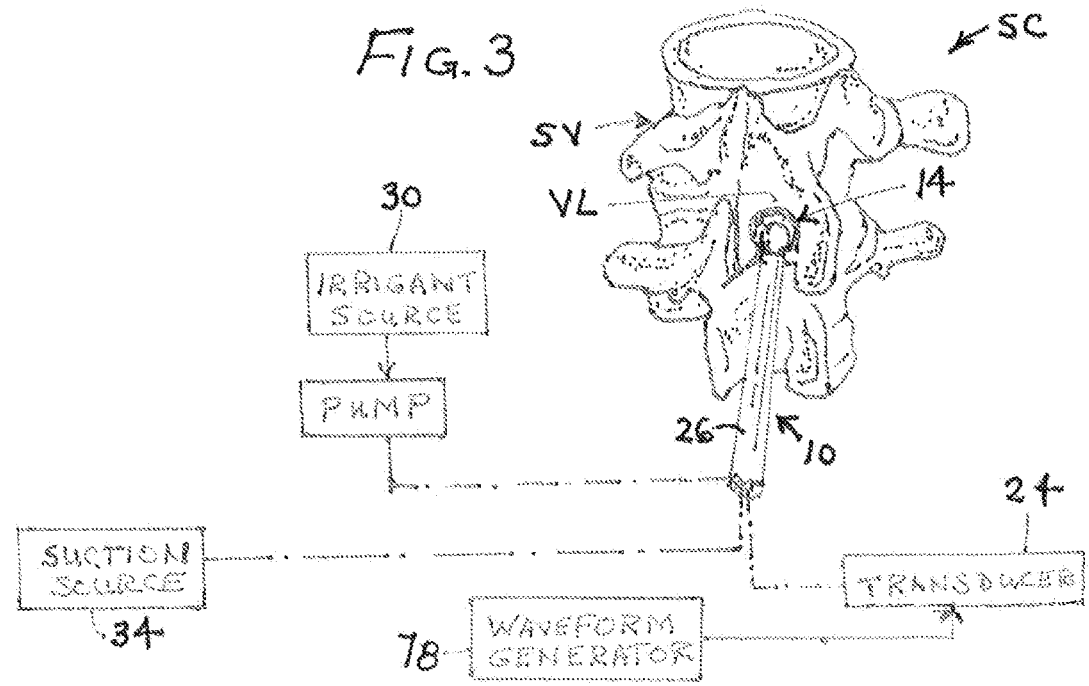
FIG. 3 is partially a schematic perspective view of two spinal vertebrae and a distal end portion of the bone shaving probe of FIG. 1 and partially a block diagram, showing a step in the surgical method of the present invention.

To remove a herniated or bulging portion HP (FIG. 4) of a vertebral disc, one first removes at least a portion of a spinal vertebra SV, typically a portion of the target vertebra's lamina VL (FIG. 3), to form an access path 76 (FIG. 4) into a vertebral foramen VF of the spinal column SC of a patient. Preferably, the selective removal of vertebral lamina VL includes manipulating an ultrasonic abrading or incising instrument such as probe 10, as illustrated in FIG. 3. A waveform generator 74 energizes transducer 24 to generate an ultrasonic standing wave in probe 10, vibrating head 14 and teeth 16 to thereby abrade and shave away the tissue of lamina VL and open up access path 76. During this procedure, pump 36 moves liquid coolant under pressure from source 30 through space 28 to probe head 14, while suction source 30 sucks a disc debris and irrigant from vertebral foramen VF through lumen 32.

After the formation of access path 76, surgical instrument or probe 40 is inserted along the path and distal end or tip 44 placed in operative contract with herniated or bulging disc material HP. Surgical instrument/probe is operated to fragment the herniated or bulging disc material HP. The resulting debris is suctioned by vacuum generator 64 out of vertebral foramen VF in a slurry of particles and liquid from source 60. The removal of herniated or bulging portion HP spaces a remaining portion of the spinal disc SD from spinal nerves (not shown) so that the potential for impingement of disc on nerves is reduced if not eliminated.

In a further surgical procedure, depicted in FIG. 5, operating or distal tip 44 of probe 40 is placed into contact with an outer surface 80 of the remaining portion of spinal disc SD. An ultrasonic mechanical standing wave is generated in probe 40, particularly including shaft 42 thereof while maintaining operative tip 44 in contact with outer surface 80 to harden the wall surface and thereby reduce chances of postoperative disc herniation at the wall surface.

The generating of the ultrasonic mechanical standing wave in probe 40 to harden disc surface 80 is preferably carried out at an ultrasonic vibratory power sufficiently low to avoid unduly damaging the spinal disc SD. In addition, the vibrating of probe 40 in this stage of a partial discectomy is optimally performed with minimal or no irrigation and little or no suction. To that end, the surgical personnel in the operating room may use individual controls 68, 70, and 72 to selectively reduce the degree of suction applied by vacuum generator 64, the rate of irrigant delivery by pump 70, and the power output of waveform generator 74, respectively. Alternatively, master control 75 may be operated to simultaneously reduce the operational performances of generator 64, pump 70, and generator 74, exemplarily by predetermined amounts so that applied ultrasonic vibratory energy is insufficient to cause disc disintegration or undue disc damage but great enough to harden surface 80 (FIG. 5).

The feeding rate of the irrigation fluid and the degree of applied suction are reduced at least 80% relative to a feeding rate of the irrigation fluid and a degree of applied suction, respectively, during the fragmentation and removal of herniated or bulging disc material HP. Thus the feeding rate of the irrigation fluid and the degree of applied suction during the disc hardening procedure of FIG. 5 are each at most 20% of the respective levels during the removal procedure of FIG. 4. In addition, power supplied to probe 40 is substantially reduced during the procedure to harden the wall surface 80. Specifically, the power of ultrasonic vibration of the ultrasonic surgical probe 40 during the generating of the ultrasonic mechanical standing wave to harden the wall surface 80 is less than 20%, preferably substantially less than 20%, exemplarily less than 10%, of the power of ultrasonic vibration of the ultrasonic surgical probe during the operating thereof to remove the herniated or bulging disc material HP.

Pursuant to the above description, the surgical instrument 40 that fragments and removes the herniated or bulging portion HP of spinal disc SD is the same instrument used to harden the newly created residual surface 80 of the spinal disc. However, it is possible to use two different instruments, one to fragment and remove herniated or bulging disc material HP and the other to harden the disc surface 80 along the vertebral foramen VF. In the former embodiment, as described above, the operating parameters of instrument or probe 40 are altered from a high-level fragmentation and debris removal operating mode to a low-level disc hardening operating mode. In the latter embodiment, the fragmentation and debris-removal instrument is withdrawn from the patient after removing of the herniated or bulging disc material HP before the ultrasonic disc-hardening surgical probe is inserted into the patient along access path 66.

As discussed above, irrigation serves in part to cool probe shafts 12 and 42 as well as surrounding sheaths 26 and 56, thereby avoiding heat damage to adjacent tissues. The irrigant also serves as a matrix or carrier to generate a slurry of organic debris that may be easily extracted from the surgical site. The generating of the ultrasonic mechanical standing wave in the ultrasonic surgical probe to harden the disc wall is carried out with substantially less irrigation and substantially less suction than that applied to the herniated or bulging disc material HP.

Figure 6:
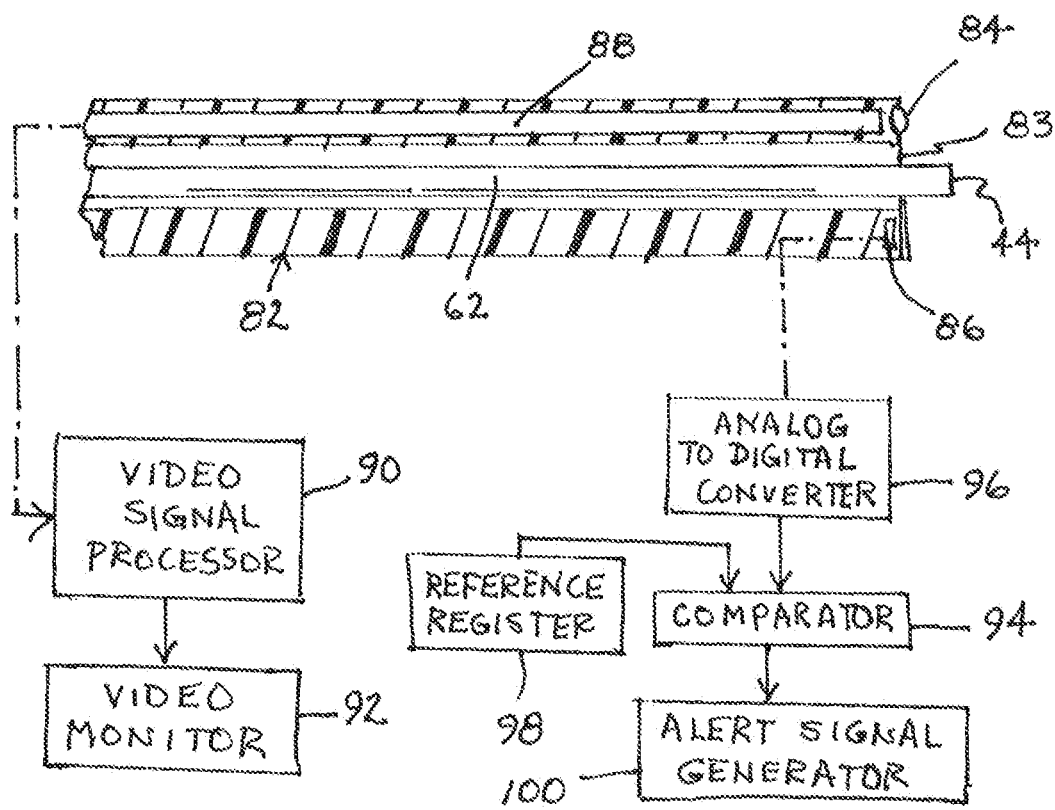
FIG. 6 is partially an enlarged partial view of a modified instrument assembly and partially a block diagram of components that may be provided for the procedure of FIG. 5 in addition to components illustrated in FIG. 4.

As illustrated in FIG. 6, sheath 56 may be replaced a sheath 82 provided at a distal end 83 with a lens 84 and/or a thermal sensor 86. Lens 84 focuses incoming electromagnetic radiation, exemplarily in the visible spectrum, onto a distal end of an optical fiber bundle 88. Sheath 82 may be further provided at distal end 83 with an illumination source (not illustrated) such as a light-emitting diode (LED). Optical fiber bundle 88 provides input to a charge coupled device (not separately illustrated) included in a signal processor 90. (The CCD may be provided at the distal end of sheath 82, just behind lens 84. In that case, optical fiber bundle 88 is replaced by an electrical conductor.) Signal processor 90 transmits a video signal to a video monitor 92 for providing an image of tissue structures at a predetermined distal from distal end 83 of sheath 82, facilitating the disc-material removal procedure of FIG. 4 and the disc-surface hardening procedure of FIG. 5.

Thermal sensor 86 is operatively connected to a digital comparator 94 via an analog-to-digital converter 96. Comparator 94 compares the digitized signal from converter 96 with at least one reference value stored in a register 98 and issues a warning signal via an alert signal generator 100 to indicate that a threshold temperature has been attained by disc material at the surgical site. For instance, signal generator 100 may produce an audible or visible indication that probe 62 has heated the disc material to a sufficient degree to cause the desired hardening. Signal generator 100 may produce a different audible or visible indication if the temperature detected by thermal sensor 86 exceeds a pre-established maximum.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A discectomy method, comprising:
   removing, by operating an ultrasonic abrading or incising instrument, at least a portion of a spinal lamina to form an access path in a patient;
   inserting an ultrasonic surgical instrument along said path so that a distal end of said ultrasonic surgical instrument is operatively engageable with herniated or bulging material of a spinal disc;
   operating said ultrasonic surgical instrument to remove the herniated or bulging disc material, to thereby space a remaining portion of said spinal disc from spinal nerves, the operating of the ultrasonic surgical instrument to remove the herniated or bulging disc material including feeding irrigation fluid and applying suction to the distal end of the ultrasonic surgical instrument during the removal of the herniated or bulging disc material;
   placing an operating tip of an ultrasonic surgical probe into contact with an outer surface of the remaining portion of said spinal disc; and
   generating an ultrasonic mechanical standing wave in said ultrasonic surgical probe while maintaining said operating tip in contact with said outer surface to harden said outer surface and thereby reduce chances of disc herniation at said outer surface,
   the generating of the ultrasonic mechanical standing wave in the ultrasonic surgical probe being carried out at an ultrasonic vibratory power sufficiently low to avoid significant damage to the spinal disc, with minimal or no irrigation fluid and little or no suction, and with substantially less irrigation fluid and substantially less suction than that fed or applied during the operating of the ultrasonic surgical instrument,
   the ultrasonic surgical instrument, the ultrasonic surgical probe, and the ultrasonic abrading or incising instrument being different from each other.

2. A discectomy method, comprising:
   removing at least a portion of a spinal lamina to form an access path in a patient;
   inserting an ultrasonic surgical probe along said path so that an operating tip of the ultrasonic surgical probe is operatively engageable with herniated or bulging material of a spinal disc;
   operating the ultrasonic surgical probe to remove the herniated or bulging disc material, to thereby space a remaining portion of said spinal disc from spinal nerves, the operating of the ultrasonic surgical probe to remove the herniated or bulging disc material including feeding irrigation fluid and applying suction to said operating tip during the removal of the herniated or bulging disc material,
   placing the operating tip of the ultrasonic surgical probe into contact with an outer surface of the remaining portion of the spinal disc;
   generating an ultrasonic mechanical standing wave in the ultrasonic surgical probe while maintaining the operating tip in contact with the outer surface to harden the outer surface and thereby reduce chances of disc herniation at the outer surface;
   substantially reducing both a feeding rate of said irrigation fluid and a degree of applied suction during the generating of said ultrasonic mechanical standing wave to harden said outer surface; and
   substantially reducing power to said ultrasonic surgical probe during the generating of said ultrasonic mechanical standing wave to harden said outer surface.

3. The discectomy method defined in claim 2, wherein the removing of said at least a portion of said spinal lamina includes operating an ultrasonic abrading or incising instrument different from said ultrasonic surgical probe.

4. The discectomy method defined in claim 2, wherein the feeding rate of said irrigation fluid and the degree of applied suction are respectively reduced at least 80% relative to a feeding rate of said irrigation fluid and a degree of applied suction during the operating of the ultrasonic surgical probe to remove the herniated or bulging disc material.

5. The discectomy method defined in claim 2, wherein the power of ultrasonic vibration of said ultrasonic surgical probe during the generating of said ultrasonic mechanical standing wave to harden said outer surface is less than 20% of the power of ultrasonic vibration of said ultrasonic surgical probe during the operating thereof to remove the herniated or bulging disc material.

6. The discectomy method defined in claim 1, further comprising removing said ultrasonic surgical instrument from the patient after removing of the herniated or bulging disc material, said ultrasonic surgical probe being inserted into the patient along said access path after removal of said ultrasonic surgical instrument.

* * * * *